US006689834B2

(12) United States Patent
Ackermann et al.

(10) Patent No.: US 6,689,834 B2
(45) Date of Patent: Feb. 10, 2004

(54) LIQUID SULFUR-CONTAINING OLIGOSILOXANES AND THEIR USE IN RUBBER MIXTURES

(75) Inventors: Jürgen Ackermann, Leverkusen (DE); Hermann-Josef Weidenhaupt, Pulheim (DE); Stefan Grabowski, Dormagen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/948,451

(22) Filed: Sep. 7, 2001

(65) Prior Publication Data
US 2002/0091187 A1 Jul. 11, 2002

(30) Foreign Application Priority Data

Sep. 11, 2000 (DE) .......................................... 10 044 989

(51) Int. Cl.$^7$ ........................ C08L 83/08; C08G 77/28; C08K 3/36
(52) U.S. Cl. ...................... 524/493; 524/492; 524/588; 528/21; 528/25; 528/30; 556/427
(58) Field of Search ..................... 556/427; 524/588, 524/492, 493; 528/21, 23, 30

(56) References Cited

U.S. PATENT DOCUMENTS

| | | | |
|---|---|---|---|
| 4,100,172 A | 7/1978 | Mui et al. ............... 260/327 H |
| 4,201,698 A | 5/1980 | Itoh et al. ....................... 260/3 |
| 4,202,831 A | 5/1980 | Schlak et al. ............... 556/467 |
| 4,254,271 A | 3/1981 | Finke et al. ................ 556/467 |
| 4,269,991 A | 5/1981 | Homan et al. .............. 556/427 |
| 4,384,132 A | 5/1983 | Schwarz et al. ............ 556/427 |
| 4,408,064 A | 10/1983 | Schwarz et al. ............ 556/427 |
| 4,444,936 A | 4/1984 | Schwarz et al. ............ 524/393 |
| 4,474,908 A | 10/1984 | Wagner ...................... 523/213 |
| 4,740,322 A | 4/1988 | DiBiase et al. ............. 252/47.5 |
| 4,831,169 A | 5/1989 | Grape et al. ................ 556/451 |
| 5,110,969 A | 5/1992 | Dittrich et al. ............. 556/427 |
| 5,409,969 A | 4/1995 | Hamada ..................... 523/213 |
| 5,496,883 A | 3/1996 | Hamada ..................... 524/492 |
| 5,663,226 A | 9/1997 | Scholl et al. ............... 524/262 |
| 5,718,782 A * | 2/1998 | Fourgon ..................... 525/237 |
| 6,033,597 A | 3/2000 | Yatsuyanagi et al. .. 252/182.17 |
| 6,121,347 A | 9/2000 | Yatsuyanagi et al. ....... 523/209 |
| 6,140,393 A | 10/2000 | Bomal et al. ............... 523/213 |
| 6,140,447 A | 10/2000 | Gay et al. ..................... 528/15 |
| 6,177,505 B1 | 1/2001 | Yatsuyanagi et al. ....... 524/506 |
| 6,268,421 B1 | 7/2001 | Dittrich et al. ............. 524/266 |
| 6,271,331 B1 | 8/2001 | Gay et al. ..................... 528/15 |
| 6,313,205 B1 * | 11/2001 | Chiron et al. ............... 524/262 |
| 6,372,843 B1 * | 4/2002 | Barruel et al. .............. 524/588 |

FOREIGN PATENT DOCUMENTS

| | | |
|---|---|---|
| CA | 2273873 | 10/1999 |
| CA | 2287652 | 4/2000 |
| DE | 29 33 247 | 3/1980 |
| DE | 299187 | 4/1992 |
| EP | 0 025 944 | 4/1981 |
| EP | 0 531 342 | 5/1996 |
| GB | 1371949 | 10/1974 |
| JP | 6-248116 | 9/1994 |
| WO | 99/02580 | 1/1999 |

\* cited by examiner

*Primary Examiner*—Jeffrey B. Robertson
(74) *Attorney, Agent, or Firm*—Joseph C. Gil; Jennifer R. Seng

(57) ABSTRACT

The invention relates to sulfur-containing oligosiloxanes which are liquid at −25–100° C., processes for their preparation and their use in silica-containing rubber mixtures which can be crosslinked with sulfur.

20 Claims, No Drawings

LIQUID SULFUR-CONTAINING OLIGOSILOXANES AND THEIR USE IN RUBBER MIXTURES

FIELD OF THE INVENTION

The invention relates to sulfur-containing oligosiloxanes which are liquid at −25–100° C., processes for their preparation and their use in silica-containing rubber mixtures which can be crosslinked with sulfur.

BACKGROUND OF THE INVENTION

Mixtures in which polymers are compounded with reinforcing silicas and sulfur-containing silanes have frequently been proposed for the preparation of rubber mixtures which are crosslinked with sulfur and have a low loss factor in mechanical damping.

Tires of low rolling resistance are those that can be produced with such low-damping rubbers. The particular requirements here during preparation of the mixture (viscosity level), the rubber properties additionally necessary, such as abrasion and wet skidding resistance, and the desired crosslinking properties (scorch resistance) impose considerable demands both on the polymers and on the fillers and the crosslinking system.

The preparation and use of sulfur-containing alkylsilanes is prior art, cf. U.S. Pat. No. 4,100,172, DD-A5-299 187, DE-A1-2 856 229, EP-A1-466 066 and EP-A1-731 824.

DE-A-28 37 117 describes the combination of sulfide-containing silanes and/or mercapto- or alkenylalkoxysilanes in silica-containing rubber mixtures as advantageous for increasing the stability to hot air, in particular of EPDM. DE-A 29 33 247 describes the use of siloxanes with SiOH or SiOR groups in rubber mixtures with silica.

U.S. Pat. No. 4,474,908 describes the combination of a crosslinking-active with a crosslinking-inactive methylalkoxysilane in order to improve the viscosity and scorch of rubber mixtures.

JP-B-62 48 116 describes rubber mixtures of polymer, carbon black and silicas treated with methylhydrogenosiloxanes and sulfur-containing silanes.

EP-A2-761 748 describes the improvement in the viscosity properties of silica-containing mixtures by admixing siloxanes with hydrogen atoms and alkoxy- and acyloxy groups and optionally, sulfur-containing silanes. The chain lengths of the silanes here is at a degree of polymerization of approx. 40. The ratio of alkenyl- or hydrogeno-siloxane radicals to methylalkoxysiloxane radicals is between 10:90 to 21:79. EP-A2-784 072 also describes mixtures of siloxanes and sulfur-containing silanes in order to lower the viscosity of the mixture.

WO 96/16125 and WO 99/02580 also describe functionalized polyorgano-siloxanes and their production and their use in rubber mixtures, it being possible for the siloxane chains to have a length of up to 300 siloxy units. Furthermore, sulfur-functional polyorganosiloxanes, their production and rubber mixtures containing the same are described in EP-A2 964021 and EP-A2 997489.

Thus, It is known to employ mixtures of siloxanes and sulfur-containing silanes. This has the following disadvantages: first, the substances must be blended very accurately by the customer by a mixing step, and next, large amounts of undesirable alcohols are released during processing due to the alkoxy and acyloxy radicals of the siloxanes, which is ecologically unacceptable.

Furthermore, it is known to produce sulfur-containing oligosiloxanes. This does, however, have the following disadvantages: the direct production from alkenyl oligosiloxanes and sulfur by the known sulfurization processes results in highly viscous and/or gelled products. Other processes are considerably more complicated.

SUMMARY OF THE INVENTION

Therefore, the object of the present invention is to provide a mixture of alkoxysiloxane and sulfur donors which is easy to meter, can be mixed homogeneously and at least, in part, does not have the disadvantages of the prior art.

This object is achieved according to the present invention by sulfur-containing siloxanes of the general formula (I)

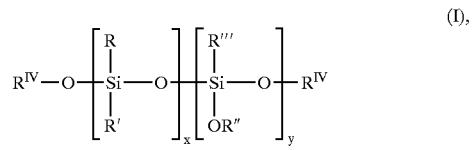

wherein
R and R" independently of one another represent a $C_1$–$C_{24}$-alkyl radical or a $C_6$–$C_{24}$-aryl radical,
R' represents a sulfur-containing 2-(p-methylcyclohexyl) propyl radical, a sulfur-containing 2-cyclohexylethyl radical, a sulfur-containing 2-norbornylethyl radical, a sulfur-containing 2-norbornylpropyl radical, a sulfur-containing $C_4$-$C_{24}$-alkyl radical or a sulfur-containing dicyclopentyl radical,
R''' represents R, OR or H, wherein the radicals R and R''' can be identical or different,
$R^{IV}$ represents R, $SiR_3'''$ or H, wherein the radicals R, R''' and $R^{IV}$ can be identical or different,
the sum of x and y is a number in the range from 2 to 200, with the proviso that always only one radical R' is present per siloxane molecule.

DETAILED DESCRIPTION OF THE INVENTION

"Sulfur-containing" means that the corresponding radicals have been formed by reaction of a double bond with sulfur and/or hydrogen sulfide. The sulfur-containing radicals, thus, carry —SH, Sx or other sulfur substituents. These can, optionally, also be coordinated associatively on the double bond. Sx here denotes sulfur chains or rings with a length in the range of 1–100 sulfur atoms.

If R' represents a sulfur-containing $C_4$–$C_{24}$-alkyl radical, the $C_4$–$C_{24}$-alkyl represents e.g. a butane, pentane, hexane, heptane, octane or nonane radical, preferably a butane, hexane or octane.

R and R" represent a $C_1$–$C_{24}$-alkyl radical, which can be present in a linear, branched or also a cyclic structure, such as methyl, ethyl, propyl, butyl, pentyl, hexyl, cyclopentyl, cyclohexyl or tert-butyl radicals. For R and R", methyl, ethyl, propyl, cyclopentyl, cyclohexyl and tert-butyl radicals are preferred, more preferably methyl, ethyl, cyclohexyl and tert-butyl radicals. The alkyl radicals can also be halogen-substituted, and Cl-methyl and Cl-propyl radicals are preferred.

R and R" can also represent a $C_6$–$C_{24}$-aryl radical, which can be substituted in its turn by the above-mentioned $C_1$–$C_{24}$-alkyl radicals or other aryl radicals, such as the phenyl, cyclopentadienyl, naphthyl, methyl-phenyl, ethylphenyl or tert-butylphenyl radical. Phenyl radicals are preferred.

The above-mentioned alkyl radicals can, of course, in their turn also be substituted again by aryl radicals, such as phenylmethyl, phenylethyl or also triphenylmethyl radicals.

The sum of x and y is a number in the range from 2 to 200, preferably 2 to 50, more preferably 2 to 20, and most preferably 2 to 10.

The x elements of the structure [RR'SiO] and the y elements of the structure [OR"R'"SiO] can, of course, each be arranged as blocks along the siloxane chain in a sequential fashion or regularly or in random distribution.

If $R^{IV}$=H or OR, cyclic condensates can be formed. If $R^{IV}$=H at both chain ends, such condensates are formed spontaneously in the mixture with the elimination of water. If at one chain end, $R^{IV}$=H and at the other chain end, $R^{IV}$=OR, such condensates are formed spontaneously in the mixture with the elimination of the alcohol ROH. If $R^{IV}$=OR at both chain ends, such condensates are formed in the mixture in the presence of catalysts and/or water, e.g. atmospheric moisture, with the elimination of the alcohol ROH.

The problem is also solved according to the present invention by sulfur-containing siloxanes (Ia) which are composed of the following structural units (K), (L), (M) and (N)

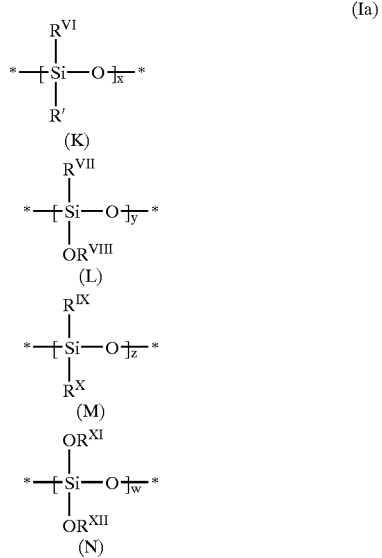

wherein
$R^{VI}$ represents a $C_1$–$C_{24}$-alkyl radical, a $C_6$–$C_{24}$-aryl radical, a $C_1$–$C_{24}$-alkoxy radical, a $C_6$–$C_{24}$-aryloxy radical, H or OH, R' has the abovementioned meaning, $R^{VII}$, $R^{VIII}$, $R^{IX}$, $R^X$, $R^{XI}$ and $R^{XII}$ independently of one another represent a $C_1$–$C_{24}$-alkyl radical, a $C_6$–$C_{24}$-aryl radical or H, the above-mentioned restrictions apply to x and y and w and z each independently of one another can be an integer between 0 and 100. The individual structural units can be arranged in succession in any desired order and linearly or cyclically. If a linear chain is present, terminal chain groups $R^{IV}$ and $OR^{IV}$ can additionally be present, wherein $R^{IV}$ has the abovementioned meaning.

The sulfur-containing siloxanes of the structure (I) according to the present invention can be present either as pure compounds or as mixtures of various compounds. In addition, the sulfur-containing siloxanes of the structure (Ia) according to the present invention can be present either as pure compounds or as mixtures of various compounds. It is, of course, also possible for mixtures of siloxanes of the structure (I) and those of the structure (Ia) to be present.

The sulfur-containing siloxanes according to the present invention can be prepared analogously to known processes, as described in U.S. Pat. No. 4,100,172 or DE-A-4 435 31 1.

However, the sulfur-containing siloxanes according to the present invention can advantageously be prepared from siloxanes of the general formula (II) and/or (IIa)

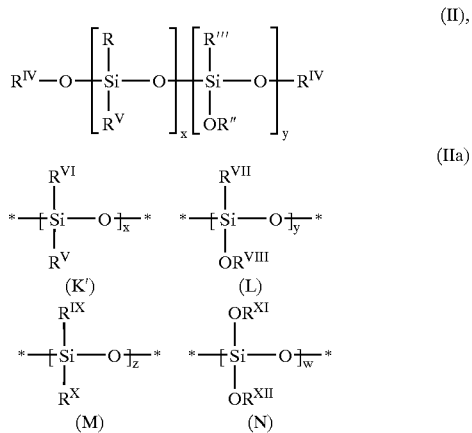

wherein
R, R", R'", $R^{IV}$, $R^{VI}$, $R^{VII}$, $R^{VIII}$, $R^{IX}$, $R^X$, $R^{XI}$ and $R^{XII}$ represent the radicals already mentioned and w and z have the above mentioned meanings and $R^V$ represents a limonyl radical, an ethylenecyclohexene radical, an ethylenenorbornenyl radical or norbornylethylidene or norbornylvinyl radical, a $C_4$–$C_{24}$-alkenyl radical or a bicyclopentenyl radical and the restriction already defined applies to the sum of x and y, with the proviso that always only one radical $R^V$ is present per molecule, the siloxanes of the general formula (II) and/or (IIa) being reacted with elemental sulfur or with a mixture of sulfur and hydrogen sulfide in the presence of a catalyst.

The sulfur-containing siloxanes of the structure (II) according to the present invention can be present either as pure compounds or as mixtures of various compounds. It is also possible for the sulfur-containing siloxanes of the structure (IIa) according to the present invention to be present either as pure compounds or as mixtures of various compounds. It is, of course, also possible for mixtures of siloxanes of the structure (I) with those of structure (Ia) to be present.

The elemental sulfur is employed in amounts in the range from 1 to 8 mol of sulfur per mol of $R^V$, preferably in amounts in the range from 1 to 6 mol of sulfur per mol of $R^V$, more preferably 1 to 4 mol of sulfur per mol of $R^V$.

If mixtures of sulfur and hydrogen sulfide are used, these are likewise employed in amounts of 1 to 8 mol of total sulfur per mol of $R^V$, preferably 1 to 6 mol of total sulfur per mol of $R^V$ and more preferably 1 to 4 mol of total sulfur per mol of $R^V$. The ratio of sulfur to $H_2S$ is 1:0.01-1, preferably 1:0.2.

Amines, mercaptobenzothiazole, salts as described in WO087/00833 p. 6, 1.24 et seq., disulfur dichloride or other catalysts known to the expert which catalyze the addition of sulfur on to double bonds can be used as the catalyst cf.

EP-A2-531 842, EP-A1-25 944, DE 2 111 842. However, amines, such as tertiary $C_{12}$–$C_{14}$-amines or mercaptobenzothiazole or disulfur dichloride are preferably used.

The catalyst is employed in amounts in the range from 0.001 to 0.1 mol per mol of sulfur, and preferably, 0.005 to 0.01 mol per mol of sulfur. Mixtures of catalysts can, of course, also be employed.

The reaction of the siloxanes (II) and/or (IIa) with sulfur or sulfur/$H_2S$ in the presence of a catalyst can be carried out in any suitable apparatus known to one skilled in the art. It is advantageous to ensure good thorough mixing.

The reaction is carried out at temperatures in the range from 0 to 200° C., preferably 120–180° C., more preferably 120–160° C.

The reaction is carried out under pressures in the range from 0 to 100 bar, preferably 0–30, more preferably 0.5–15.

The present invention also provides both the siloxanes of the general formula (II) and/or (IIa) described and the processes described for their reaction with sulfur or sulfur/$H_2S$.

The siloxanes of the formula (II) and/or (IIa) according to the present invention can, in principle, be prepared by customary methods described in the literature. See, for example, EP-A1 2 59 625, EP-A1 4310 and EP-A1 3 514.

The siloxanes of the general formula (II) according to the present invention can advantageously be prepared from siloxanes of the general formula (III)

$$R^{IV}-O-\left[\begin{array}{c}R\\|\\Si\\|\\H\end{array}-O\right]_x\left[\begin{array}{c}R'''\\|\\Si\\|\\H\end{array}-O\right]_y-R^{IV} \quad (III),$$

wherein the radicals have the meaning already mentioned and x+y represents a number in the range of 2–200, preferably 2–50, more preferably 2–20, and most preferably 2–10.

Accordingly, the siloxanes of the general formula (IIa) according to the present invention can advantageously be prepared from siloxanes of the general formula (IIIa)

$$\begin{array}{c}
R^{VI}\\|\\
*-\!\!\left[Si-O\right]_x\!\!-\!*\\|\\
H\\
(K'')\\
R^{VII}\\|\\
*-\!\!\left[Si-O\right]_y\!\!-\!*\\|\\
H\\
(L')\\
R^{IX}\\|\\
*-\!\!\left[Si-O\right]_z\!\!-\!*\\|\\
R^X\\
(M)\\
OR^{XI}\\|\\
*-\!\!\left[Si-O\right]_w\!\!-\!*\\|\\
OR^{XII}\\
(N)
\end{array} \quad (IIIa)$$

wherein
the radicals have the meanings already mentioned and the restrictions mentioned apply to x+y, z and w.

The siloxanes (III) and/or (IIIa) are reacted here with alcohols and dienes in the presence of a catalyst.

Any alcohol known to the expert is possible here, in principle, as the alcohol, and examples which may be mentioned are $C_1$–$C_{24}$-alcohols, such as methanol, ethanol, propanol, butanol, pentanol, hexanol, heptanol, octanol, decanol, phenol, in particular methanol, ethanol, propanol and butanol, very particularly preferably ethanol and propanol.

The dienes corresponding to $R^V$ are employed as the diene. These are limonene, vinylcyclohexene, ethylidenenorbornene, vinylnorbornene and $C_4$–$C_{24}$-dienes, preferably, butadiene, hexadiene, heptadiene, octadiene and bicyclopentadiene.

All the catalysts known to the expert which catalyze the substitution of hydridic hydrogen atoms on silicon atoms by dienes are possible as the catalyst, in particular platinum, rhodium, ruthenium or nickel, and salts and/or complexes thereof.

The catalyst is employed in amounts in the range of 1–100 ppm of metal, based on the total amount of diene and siloxane, preferably 5 to 500 ppm, and most preferably 10–50 ppm.

The ratio of OR" to $R^V$ is determined by the stoichiometric ratio of the alcohol to diene and the sequence of addition of the educts.

The siloxanes (III) and/or (IIIa) are preferably reacted first with the alcohol and then with the diene. Furthermore, the siloxanes (III) are preferably reacted simultaneously with the alcohol and the diene.

It is, of course, also possible to employ mixtures of different alcohols and/or mixtures of different dienes.

The reaction is carried out at temperatures in the range from −20 to +200° C., preferably 20–100° C.

The reaction is carried out under pressures of 0 to 50 bar, preferably 0–5 bar.

The reaction can be carried out in any apparatus suitable for hydrosilylation reactions which is known to one skilled in the art.

The reaction products are optionally purified, for example, by distillation, optionally under reduced pressure or by another suitable process, in order to remove excess, non-reacted substances and secondary products.

The present invention also provides the use of the sulfur-containing siloxanes of the general formula (I) and/or (Ia) and of the siloxanes of the general formula (II) and/or (IIa) in silica-containing rubber mixtures.

Additionally, the present invention also provides a mixture of the sulfur-containing siloxanes of the general formula (I) according to the present invention with siloxanes and/or sulfur-containing silanes of the prior art. The siloxanes and/or sulfur-containing silanes described in U.S. Pat. No. 4,100,172, EP-A 1 466 066, DE-A 2 837 117, DE-A 2 933 247, U.S. Pat. No. 4,474,908, JP-A 6 248 116, EP-A 1 761 748 and EP-A 1 784 072 e.g. are possible here.

The sulfur-containing siloxanes (I) and/or (Ia) can also be employed as a mixture with the siloxanes (II) and/or (IIa).

If the siloxanes of the general formula (II) and/or (IIa) are used without the sulfur-containing siloxanes of the general formula (I) and/or (Ia), sulfur-containing alkoxysiloxanes, which have in the molecule at least one alkoxy radical which is capable of reacting with the Si—OH groups of the silica surface under the mixing conditions and which carry in the molecule at least one sulfur-containing radical which is capable of reacting with the unsaturated rubber under the mixing or vulcanization conditions must furthermore be employed.

Preferred sulfur-containing alkoxysiloxanes in this case are, in particular, bis-(trialkoxysilyl-alkyl) polysulfides, as described in DE 2 141 159 and DE-AS 2 255 577, and oligomeric and/or polymeric sulfur-containing alkoxysilanes of DE-OS 4 435 311 and EP-A 670 347.

The sulfur-containing alkoxysilanes are then employed in amounts of 0.1 to 20 parts by wt., preferably 0.5 to 10 parts by wt., based on 100 parts by wt. of rubber.

Silicas, which are employed for the silica-containing rubber mixtures are:

- silicas prepared by precipitation of solutions of silicates with spec. surface areas of 30 to 1,000, preferably 30 to 400 $m^2/g$ (BET surface area) and with primary particle sizes of 10 to 400 nm. The silicas can optionally also be present as mixed oxides with other metal oxides, such as oxides of aluminum, magnesium, calcium, barium, zinc, zirconium or titanium;
- silicates, e.g. aluminum silicate and alkaline earth metal silicates, such as magnesium silicate or calcium silicate, with BET surface areas of 30 to 400 $m^2/g$ and primary particle diameters of 10 to 400 nm.

Such products are described in more detail, for example, in J. Franta, Elastomers and Rubber Compounding Materials, Elsevier 1989, pages 401–447.

Suitable rubbers are, in addition to natural rubber, also the known synthetic rubbers. They include, inter alia, polybutadiene, butadiene/acrylic acid $C_1$–$C_4$-alkyl ester, polychloroprene, polyisoprene and polyisoprene copolymers, styrene/butadiene copolymers with styrene contents of 1 to 60, preferably 20 to 50 wt. %, styrene/butadiene copolymers with 1–20 wt. % of further polar unsaturated monomers, in particular styrene/butadiene/acrylonitrile copolymers with styrene contents of 1 to 40% and acrylonitrile contents of up to 20%, isobutylene/isoprene copolymers, butadiene/acrylonitrile copolymers with acrylonitrile contents of 5 to 60, preferably 10 to 40 wt. %, partly hydrogenated or completely hydrogenated NBR rubber, ethylene/propylene/diene copolymers and mixtures of these rubbers.

Natural rubber, BR, SBR and styrene/butadiene/acrylonitrile copolymers are preferred, in particular, for the production of motor vehicle tires with the aid of the sulfur-containing siloxanes of the general formula (I) according to the present invention or siloxanes of the general formula (II) according to the present invention.

Preferred ratios of rubber to silica are 100:10 to 100:150, more preferably 100:20 to 100:100.

Carbon blacks and the conventional rubber auxiliaries, such as e.g. stabilizers, mold release agents, plasticizers etc., can moreover be added.

The amounts of rubber auxiliaries added depends on the particular intended use. Preferred amounts of carbon blacks are 0 to 30 parts by wt., amounts of stabilizers are 0.1 to 1.5 parts by wt., and amounts of plasticizers are 5 to 75 parts by wt. per 100 parts by wt. of rubber. Mineral oil plasticizers are to be understood as meaning paraffinic, naphthenic or aromatic mineral oils with VDC numbers (viscosity-density constants) of 0.791 to 1.050, preferably 0.85 to 1.0, and refraction intercepts $R_i$ of approx. 1.048 to 1.065.

Such mineral oil plasticizers are commercially obtainable. Aromatic mineral oil plasticizers are preferred plasticizers.

The rubber mixtures can be prepared in a conventional manner, e.g. by means of kneaders, roll mills or extruders.

The rubber mixtures can optionally also comprise further fillers, such as

- naturally occurring silicates, such as kaolin and other naturally occurring silicas;
- glass fibers and glass fiber products (mats, strands) or glass microbeads;
- metal oxides, such as zinc oxide, calcium oxide, magnesium oxide or aluminum oxide;
- metal carbonates, such as magnesium carbonate, calcium carbonate or zinc carbonate;
- metal hydroxides, such as e.g. aluminum hydroxide or magnesium hydroxide;
- carbon blacks; the carbon blacks to be used here are prepared by the flame black or furnace or gas black process and have BET surface areas of 20 to 200 $m^2/g$, such as e.g. SAF, ISAF, HAF, FEF or GPF carbon blacks.

Highly dispersed precipitated silicas and carbon blacks are preferably employed. The fillers mentioned can be employed by themselves or as a mixture.

Moreover, further rubbers can be admixed to the rubber mixtures in a conventional manner: Natural rubber, emulsion SBR and solution SBR rubbers with a glass transition temperature above −50° C., which can optionally be modified with alkoxysilane or other functional groups, as described e.g. in EP-A 447 066, polybutadiene rubbers with a high 1,4-cis content (>90%), which are prepared with catalysts based on Ni, Co, Ti or Nd, and polybutadiene rubbers with a vinyl content of 0 to 75% and mixtures thereof are of interest in particular for the production of motor vehicle tires. Solution SBR rubbers with a vinyl content of 20 to 60 wt. % and polybutadiene rubbers with a high 1,4-cis content (>90%) are preferably employed.

The rubber mixtures can, of course, also additionally comprise further rubber auxiliary products which are known and conventional in the rubber industry, such as reaction accelerators, anti-aging agents, heat stabilizers, light stabilizers, ozone stabilizers, processing auxiliaries, plasticizers, tackifiers, blowing agents, dyestuffs, pigments, waxes, extenders, organic acids, retardants, metal oxides and activators, such as triethanolamine, polyethylene glycol and hexanetriol. The rubber auxiliaries are admixed in the conventional amounts and depend on the particular intended use envisaged. Conventional amounts are, for example, amounts of 0.1 to 50 wt. %, based on the total amount of rubber employed.

In addition to the above-mentioned rubber auxiliary products, the known crosslinking agents, such as sulfur, sulfur donors or peroxides, can be added to the rubber mixtures according to the present invention. The rubber mixtures according to the present invention can, moreover, comprise vulcanization accelerators, such as mercaptobenzothiazoles, mercaptosulfenamides, guanidines, thiurams, dithiocarbamates, thioureas and/or thiocarbonates. The vulcanization accelerators and the crosslinking agents mentioned are conventionally employed in amounts of 0.1 to 10 wt. %, preferably 0.1 to 5 wt. %, based on the total amount of the particular rubber employed.

The vulcanization of the rubber mixtures according to the present invention can be carried out at conventional temperatures of 100 to 200° C., preferably 130 to 180° C. (optionally under a pressure of 10 to 200 bar).

Further blending of the rubbers with the other rubber auxiliary products, crosslinking agents and accelerators mentioned can be carried out in a conventional manner with the aid of suitable mixing units, such as roll mills, internal mixers and mixing extruders.

The rubber vulcanization products, which can be prepared from these, are suitable for the production of all types of shaped articles, e.g. for the production of cable sheathings, hoses, drive belts, conveyor belts, roller coverings, shoe soles, sealing rings and damping elements. They are particularly suitable for the production of tires, since such tires have a particularly low rolling resistance, a particularly good wet skidding resistance and a high abrasion resistance.

The following examples illustrate the invention in more detail.

EXAMPLES

The rubber polymers and chemicals are commercial products from Bayer AG Rubber Business Unit, unless stated otherwise. The rubber-mechanical tests were carried out in accordance with DIN 53523, 53504, 53505, 53512, 53513 and ASTM D 2084.

Example 1

Preparation of the sulfur-containing siloxanes of the general formula (I)/(Ia).

Example 1a

In a four-necked flask with a nitrogen inlet, thermometer, stirrer and a reflux condenser connected to a gas washer (charged with 750 ml 30% aqueous NaOH), under a nitrogen atmosphere, 250 g of the alkenylalkoxysiloxane mixture.

| Mol % | Chemical name |
|---|---|
| 11 | Tetraethyloxysilane |
| 6.8 | methyl-(2-cyclohexenyl-ethyl)-diethoxy-silane |
| 24.9 | 1-methyl-1-(2-cyclohexenyl-ethyl)-1,3,3,3-tetraethoxy-disiloxane |
| 13 | 2-methyl-2-(2-cyclohexenyl-ethyl)-1,1,1,5,5,5-hexaethoxy- |
| 8.4 | trisiloxane |
| 17.4 | 1,3-dimethyl-1,3-bis-(2-cyclohexenyl-ethyl)-1,3-diethoxy-disiloxane |
| 7.5 | 1,3-dimethyl-1,3-bis-(2-cyclohexenyl-ethyl)-1,5,5,5-tetraethoxy-trisiloxane |
| 4.2 | 3,5-dimethyl-3,5-bis-(2-cyclohexenyl-ethyl)-1,1,1,5,5,5-hexaethoxy-tetrasiloxane |

-continued

| Mol % | Chemical name |
|---|---|
| 6.8 | 1,3,5-trimethyl-1,3,5-tris-(2-cyclohexenyl-ethyl)-1,3-diethoxy-trisiloxane |
|  | 1,3,5-trimethyl-1,3,5-tris-(2-cyclohexenyl-ethyl)-1,7,7,7-tetraethoxy-tetrasiloxane | with a double bond content of 3.47 mmol/g were initially introduced ($^1$H-NMR). 83.4 g (2.60 mol) sulfur and 0.8 g tert-dodecylamine and 1.7 g mercapto-benzothiazole were added at initially 25° C.

The mixture was then heated to 150° C. and kept at 150° C. under a slightly reduced pressure of 800 hPa for 1.5 h. Gaseous constituents were then removed by degassing at 90° C. under 20–30 hPa for 45 min. The crude product was charged with nitrogen and allowed to cool to room temperature. Dried toluene was then added in a mixing ratio of 1:1 (parts by volume) and the mixture was left to stand for 8 h.

The sulfur, which had precipitated out, was filtered off with suction and washed with a little dried toluene on a closed suction filter. The desired siloxane was obtained after the combined toluene fractions had been evaporated completely in a rotary evaporator at 50° C. under 20 mbar. 280.1 g of product with a sulfur content of 19.9% were obtained. The sulfur content was determined by means of elemental analysis. The viscosity was 1,776 mPas at 23° C. and was determined by means of a Brookfield rotary viscometer.

The experiment shows that gel-free material was formed. It is obvious that gelling may occur when the alkenyl groups per Si chain are increased.

The experiments show that for the preparation of gel-free, liquid sulfur-containing oligosiloxanes, a high content of the compounds according to the present invention having only one double-bond-containing radical per siloxane chain is advantageous This correlation is further illustrated by the following example:

Example 1b–1d:

TABLE 1

| | technical siloxane mixture; formula (II) | | | | catalyst | | reaction | | | product; formula (I) | | | |
|---|---|---|---|---|---|---|---|---|---|---|---|---|---|
| | | DB | sulfur | | t- | | | conditions | | | sulfur- | bound sulfur | |
| | composition[1] (GC) | content[2] [mmol/g] | amount [g] | amount [g] | dodecyl-amine [g] | MBT [g] | T [° C.] | t [h] | p [bar] | yield [g] | content [%] | per DB [mol/mol] | viscosity [mPas] |
| 1b | 65:35 | 3.0 | 150 | 32.6 | 0.80 | 0.90 | 145 | 6.5 | 1 | 173.8 | 14.9 | 1.55 | 425 |
| 1c | 91:9 | 2.6 | 120 | 26.1 | 0.64 | 0.70 | 145 | 6.5 | 1 | 135.2 | 12.8 | 1.53 | 47 |
| 1d | 0:100 | 3.2 | 150 | 32.6 | 0.80 | 0.90 | 145 | 5.5[3] | 1 | 173.1 | 17.0 | 1.60 | solid gel |

[1]Sum of parts according to this invention containing only one residue $R^V$ per molecule in relation to the sum of parts containing more than one residue $R^V$ per molecule.
[2]DB (= double bond) content calculated from iodine number (Wijs method; DIN 53241-1)
[3]The experiment was stopped at that time; the product had solidified completely.

The experiments show that a high content of compounds according to this invention, containing only one residue with double bonds per siloxane chain, is advantageous in order to obtain gel free, liquid, sulfur-containing oligosiloxanes.

Gelled products are of only limited use in the rubber mixing process, since they can include relatively large, undefined or varying amounts of sulfur and result in non-homogeneous rubber mixtures.

Example 2

Preparation of the mixture.

In a 1.5 l internal mixer from Werner & Pfleiderer (model GK 1.5 E), the constituents of polymers, fillers and additives were initially introduced in the following manner:

TABLE 2

|  | Mixing time in min |
|---|---|
| Polymer | 0.5 min |
| Filler, anti-ageing agent, ZnO, Wax, silane, oil | 3.0 min |
| Dispersing | 1.5 min |
| Scouring of plunger | 0.25 min |
| Mixing | 1.25 min |
| Total mixing time | 6.5 min |

The ejection temperature was 140–160° C.

Thereafter, the mixture was cooled on a roll mill and then mixed again in the kneader for 3.5 min. Sulfur and accelerator were then subsequently mixed in on a roll mill at approx. 60 to 90° C.

| Components employed: | |
|---|---|
| Si 69 | bis (triethoxysilylpropyl) tetrasulfane from DEGUSSA-Hüls AG |
| Vulkanox ® 4020 | phenylenediamine product from Bayer AG |
| Vulkanox ® HS | dihydroquinoline (polymerized) product from Bayer AG |
| Vulkacit ® CZ | sulfenamide product from Bayer AG |
| Vulkacit ® D | diphenylguanidine product from Bayer AG |
| Enerthene 1849-1 | BP Deutschland GmbH |
| Antilux ® 654 | paraffinic microwax product from Rhein Chemie Rheinau |
| Vulkasil ® S | precipitated silica product from Bayer AG |
| Buna ® VSL 5025 | SSBR product from Bayer AG |
| Buna ® CB 24 | polybutadiene product from Bayer AG |
| Corax N 339 | carbon black from Degussa AG |
| Stearic acid | product from Henkel KGaA |
| ZnO RS | product from Zinkweilβ Forschungsgesellschaft |

The particular composition of the mixture is stated in the following table 3:

TABLE 3

| Example 2 | a | b |
|---|---|---|
| Buna VSL 5025-1 | 96 | 96 |
| Buna CB 24 | 30 | 30 |
| Corax N 339 | 6.5 | 6.5 |
| Vulkasil S | 80 | 80 |
| Stearic acid | 1 | 1 |
| ZnO RS | 2.5 | 2.5 |
| Enertherne 1849-1 | 8 | 8 |
| Vulkanox 4020 | 1 | 1 |
| Vulkanox HS | 1 | 1 |
| Antilux 654 | 1.5 | 1.5 |
| Sulfur | 1.5 | 1.5 |
| Vulkacit CZ | 1.5 | 1.5 |
| Vulkacit D | 2 | 2 |
| Si 69 | 6.5 |  |
| Product of Example 1 |  | 6.5 |

Production of Test Specimens

Various test specimens were produced in a manner conventional for the expert in a pressed vulcanization at 160° C.

Test specimens were then stamped out of these sheets in the conventional manner in order to carry out the rubber-mechanical testing mentioned in Example 2.

The rubber-mechanical properties of mixtures 2a–b are listed in the following Table 4.

TABLE 4

| Example 2 |  | a | b |
|---|---|---|---|
| ME (DIN 53 523) | ME | 78.9 | 88.1 |
| 5ME + min | min | 15 | 12.8 |
| ts 01 | min | 0.33 | 0.18 |
| t90 | min | 16.40 | 19.38 |
| M 100% (DIN 53 504) | MPas | 2.7 | 2.1 |
| M 300% (DIN 53 504) | MPas | 10.5 | 8.9 |
| Tensile strength (DIN 53 504) | MPas | 18.8 | 20.2 |
| Elongation (DIN 53 504) | MPas | 470 | 540 |
| Hardness 23° C. (DIN 53 505) | °Sha | 72 | 68 |
| Hardness 70° C. (DIN 53 512) | °Sha | 68 | 64 |
| RP 23° C. (DIN 53 512) |  | 27 | 26 |
| RP 70° C. (DIN 53 512) |  | 50 | 50 |
| WRF DIN 53 515 23° C. | N/mm | 53 | 42 |
| Abrasion DIN 53 516 | mm³ | 87 | 86 |
| Damping DIN 53 513 Roelig |  |  |  |
| tan δ 0° C. |  | 0.384 | 0.424 |
| tan δ 60° C. |  | 0.164 | 0.154 |

A low mechanical damping (tan δ) at 60° C. and a sharp change in the tan δ value between 0–60° C. generally apply as criteria for vulcanization products in order to achieve a low rolling resistance and other optimized tire properties.

The mixtures according to the present invention have the following advantages compared with the prior art:

1. higher reinforcing effect (ratio of modulus 300/modulus 100);
2. same abrasion;
3. lower tan delta at 60° C. and therefore, lower rolling resistance.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Sulfur-containing siloxanes of the general formula

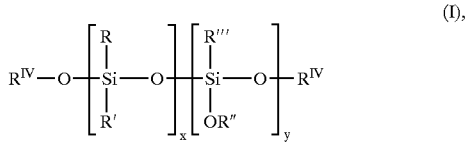

(I), wherein

R and R″ independently of one another represent a $C_1$–$C_{24}$-alkyl radical or a $C_6$–$C_{24}$-aryl radical, R′ represents a sulfur-containing 2-(p-methylcyclohexyl)propyl radical, a sulfur-containing 2-cyclohexylethyl radical, a sulfur-containing 2-norbornylethyl radical, a sulfur-containing 2-norbornylpropyl radical, a sulfur-containing $C_4$–$C_{24}$-alkyl radical or a sulfur-containing dicyclopentyl radical, wherein the sulfur containing radical does not carry SH, R‴ represents R, OR or H, wherein the radicals R and R‴ can be identical or different, $R^{IV}$ represents R, SiR₃‴ or H, wherein the radicals R, R‴ and $R^{IV}$ can be identical or different, the sum of x and y is a number in the range from 2 to 200, with the proviso that always only one radical R' is present per siloxane molecule.

2. A process for the preparation of sulfur-containing siloxanes comprising the step of reacting siloxanes of the general formula (II)

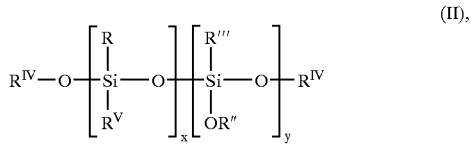
(II), wherein

R and R' independently of one another represent a $C_1$–$C_{24}$-alkyl radical or a $C_6$–$C_{24}$-aryl radical, R''' represents R, OR or H, wherein the radicals R and R''' can be identical or different, $R^{IV}$ represents R, $SiR_3$''' or H, wherein the radicals R, R''' and $R^{IV}$ can be identical or different, and $R^V$ represents a limonyl radical, an ethylenecyclohexene radical, an ethylenenorbornenyl radical or norbornylethylidene or norbornylvinyl radical, a $C_4$–$C_{24}$-alkenyl radical or a bicyclopentenyl radical and the sum of x and y is a number In the range from 2 to 200, with the proviso that always only one radical $R^V$ is present per molecule, with sulfur or with sulfur and hydrogen sulfide, in each case in the presence of a catalyst, wherein said sulfur-containing siloxanes are of the general formula (I)

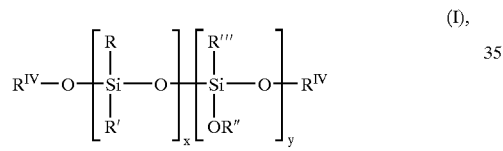
(I), wherein

R' represents a sulfur-containing 2-(p-methylcyclohexyl) propyl radical, a sulfur-containing 2-cyclohexylethyl radical, a sulfur-containing 2-norbornylethyl radical, a sulfur-containing 2-norbornylpropyl radical, a sulfur-containing $C_4$–$C_{24}$-alkyl radical or a sulfur-containing dicyclopentyl radical, wherein the sulfur containing radical does not carry SH, with the proviso that always only one radical R' is present per siloxane molecule.

3. A process according to claim 2, wherein sulfur is employed in amounts in the range from 1 to 8 mol per mol of $R^V$.

4. A process according to claim 2, wherein a mixture of sulfur and hydrogen sulfide in amounts in the range from 1 to 8 mol of total sulfur per mol of $R^V$ is employed.

5. A process according to claim 2, wherein a mixture of sulfur and hydrogen sulfide in a ratio of 1: (0.01 to 1) is employed.

6. A process according to claim 2, wherein amines or disulfur dichloride or mercaptobenzothiazole are employed as the catalyst.

7. A process according to claim 2, wherein the catalyst is employed in amounts in the range from 0.001 to 0.1 mol per mol of sulfur.

8. A mixture comprising i) sulfur-containing siloxanes of the general formula (I)

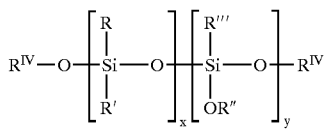
(I), wherein

R and R'' independently of one another represent a $C_1$–$C_{24}$-alkyl radical or a $C_6$–$C_{24}$-aryl radical, R' represents a sulfur-containing 2-(p-methylcyclohexyl) propyl radical, a sulfur-containing 2-cyclohexylethyl radical, a sulfur-containing 2-norbornylethyl radical, a sulfur-containing 2-norbornylpropyl radical, a sulfur-containing $C_4$–$C_{24}$-alkyl radical or a sulfur-containing dicyclopentyl radical, wherein the sulfur containing radical does not carry SH, R''' represents R, OR or H, wherein the radicals R and R''' can be identical or different, $R^{IV}$ represents R, $SiR_3$''' or H, wherein the radicals R, R''' and $R^{IV}$ can be identical or different, the sum of x and y is a number in the range from 2 to 200, with the proviso that always only one radical R' is present per siloxane molecule and siloxanes and/or sulfur-containing silanes.

9. Silica-containing rubber mixtures comprising sulfur-containing siloxanes of the general formula (I)

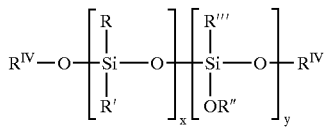
(I), wherein

R and R'' independently of one another represent a $C_1$–$C_{24}$-alkyl radical or a $C_6$–$C_{24}$-aryl radical, R' represents a sulfur-containing 2-(p-methylcyclohexyl) propyl radical, a sulfur-containing 2-cyclohexylethyl radical, a sulfur-containing 2-norbornylethyl radical, a sulfur-containing 2-norbornylpropyl radical, a sulfur-containing $C_4$–$C_{24}$-alkyl radical or a sulfur-containing dicyclopentyl radical, wherein the sulfur containing radical does not carry SH, R''' represents R, OR or H, wherein the radicals R and R''' can be identical or different, $R^{IV}$ represents R, $SiR_3$''' or H, wherein the radicals R, R''' and $R^{IV}$ can be identical or different, the sum of x and y is a number in the range from 2 to 200, with the proviso that always only one radical R' is present per siloxane molecule.

10. Silica-containing rubber mixtures according to claim 9, comprising silicas with BET-surface areas of more than 30 $m^2$/g and optionally, carbon blacks.

11. Sulfur-containing siloxanes of the general formula (Ia), comprising the structural units (K), (L), (M), (N)

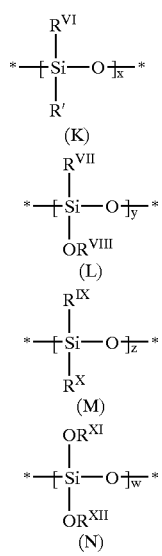
(K)

(L)

(M)

(N)

wherein
R' represents a sulfur-containing 2-(p-methylcyclohexyl) propyl radical, a sulfur-containing 2-cyclohexylethyl radical, a sulfur-containing 2-norbornylethyl radical, a sulfur-containing 2-norbornylpropyl radical, a sulfur-containing $C_4$–$C_{24}$-alkyl radical or a sulfur-containing dicyclopentyl radical, wherein the sulfur containing radical does not carry SH, $R^{VI}$ represents, $C_6$–$C_{24}$-alkyl radical, a $C_1$–$C_{24}$-aryl radical, a $C_1$–$C_{24}$-alkoxy radical, a $C_6$–$C_{24}$-aryloxy radical, H or OH, $R^{VII}$, $R^{VIII}$, $R^{IX}$, $R^X$, $R^{XI}$ and $R^{XII}$ independently of one another represent a $C_1$–$C_{24}$-alkyl radical, a $C_6$–$C_{24}$-aryl radical or H, the sum of x and y represents an integer in the range from 2 to 200 and w and z each independently of one another can be an integer between 0 and 100, with the proviso that always only one radical R' is present per siloxane molecule.

12. A process for preparing sulfur-containing siloxanes of the general formula (Ia), wherein the sulfur containing siloxanes comprise the structural units (K), (L), (M), (N)

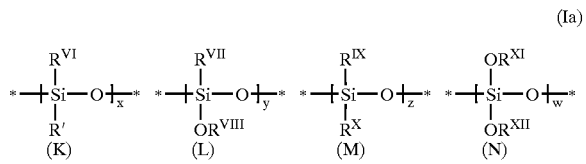

wherein
R' represents a sulfur-containing 2-(p-methylcyclohexyl) propyl radical, a sulfur-containing 2-cyclohexylethyl radical, a sulfur-containing 2-norbornylethyl radical, a sulfur-containing 2-norbornylpropyl radical, a sulfur-containing $C_4$–$C_{24}$-alkyl radical or a sulfur-containing dicyclopentyl radical, $R^{VI}$ represents a $C_1$–$C_{24}$-alkyl radical, a $C_6$–$C_{24}$-aryl radical, a $C_1$–$C_{24}$-alkoxy radical, a $C_6$–$C_{24}$-aryloxy radical, H or OH, $R^{VII}$, $R^{VIII}$, $R^{IX}$, $R^X$, $R^{XI}$ and $R^{XII}$ independently of one another represent a $C_1$–$C_{24}$-alkyl radical, a $C_6$–$C_{24}$-aryl radical or H, the sum of x and y represents an integer in the range from 2 to 200 and w and z each independently of one another can be an integer between 0 and 100, with the proviso that always only one radical R' is present per siloxane molecule, comprising the step of reading i) siloxanes of the general formula (IIa) containing structural units (K'), (L), (M), (N)

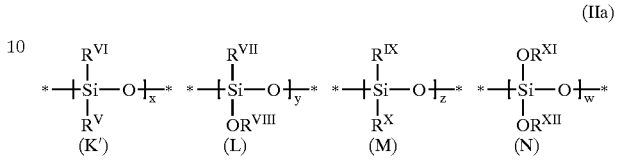

wherein
$R^V$ represents a limonyl radical, an ethylenecyclohexene radical, an ethylenenorbornenyl radical or a norbornyl-ethylidene or norbornylvinyl radical, a $C_4$–$C_{24}$-alkenyl radical or a bicyclopentenyl radical and with the proviso that always only one radical $R^V$ is present per molecule, with ii) sulfur or sulfur and hydrogen sulfide in the presence of a catalyst.

13. A process according to claim 12, wherein sulfur is employed in amounts in the range from 1 to 8 mol per mol of $R^V$.

14. A process according to claim 12, wherein a mixture of sulfur and hydrogen sulfide in amounts in the range from 1 to 8 mol of total sulfur per mol of $R^V$ is employed.

15. A process according to claim 12, wherein a mixture of sulfur and hydrogen sulfide in a ratio of 1:0.01 to 1 is employed.

16. A process according to claim 12, wherein amines or disulfur dichloride or mercaptobenzothiazole are employed as the catalyst.

17. A process according to claim 12, wherein the catalyst is employed in amounts in the range from 0.001 to 0.1 mol per mol of sulfur.

18. A mixture comprising:
i) sulfur-containing siloxanes of the general formula (Ia), comprising the structural units (K), (L), (M), (N)

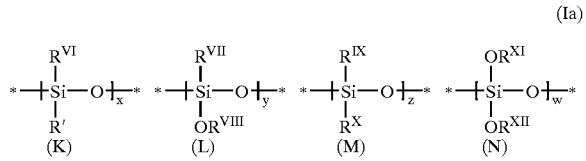

wherein
R' represents a sulfur-containing 2-(p-methylcyclohexyl) propyl radical, a sulfur-containing 2-cyclohexylethyl radical, a sulfur-containing 2-norbornylethyl radical, a sulfur-containing 2-norbornylpropyl radical, a sulfur-containing $C_4$–$C_{24}$-alkyl radical or a sulfur-containing dicyclopentyl radical, wherein the sulfur containing radical does not carry SH, $R^{VI}$ represents a $C_1$–$C_{24}$-alkyl radical, a $C_6$–$C_{24}$-aryl radical, a $C_1$–$C_{24}$-alkoxy radical, a $C_6$–$C_{24}$-aryloxy radical, H or OH, $R^{VII}$, $R^{VIII}$, $R^{IX}$, $R^X$, $R^{XI}$ and $R^{XII}$ independently of one another represent a $C_1$–$C_{24}$-alkyl radical, a $C_6$–$C_{24}$-aryl radical or, the sum of x and y represents an integer in the range from 2 to 200 and w and z each independently of one another can be an integer between 0 and 100, with the proviso that always only one radical R'is present per siloxane molecule; and ii) siloxanes and/or sulfur-containing silanes.

19. Silica-containing rubber mixtures comprising sulfur-containing siloxanes of the general formula (Ia), comprising the structural units (K), (L), (M), (N)

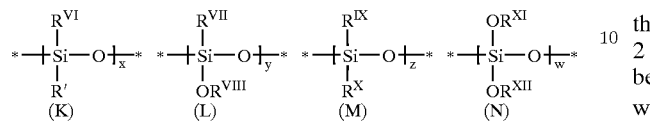

(Ia)

wherein

R' represents a sulfur-containing 2-(p-methylcyclohexyl) propyl radical, a sulfur-containing 2-cyclohexylethyl radical, a sulfur-containing 2-norbornylethyl radical, a sulfur-containing 2-norbornylpropyl radical, a sulfur-containing $C_4$–$C_{24}$-alkyl radical or a sulfur-containing dicyclopentyl radical, wherein the sulfur containing radical does not carry SH, $R^{VI}$ represents a $C_1$–$C_{24}$-alkyl radical, a $C_6$–$C_{24}$-aryl radical, a $C_1$–$C_{24}$-alkoxy radical, a $C_6$–$C_{24}$-aryloxy radical, H or OH, $R^{VII}$, $R^{VIII}$, $R^{IX}$, $R^X$, $R^{XI}$ and $R^{XII}$ independently of one another represent a $C_1$–$C_{24}$-alkyl radical, a $C_6$–$C_{24}$-aryl radical or H, the sum of x and y represents an integer in the range from 2 to 200 and w and z each independently of one another can be an integer between 0 and 100, with the proviso that always only one radical R' is present per siloxane molecule.

20. Silica-containing rubber mixtures according to claim 19, wherein the silica-containing rubber mixtures contain sillcas with BET surface areas of greater than 30 $m^2/g$ and optionally carbon blacks.

* * * * *